United States Patent [19]

Kurono et al.

[11] Patent Number: 4,906,477

[45] Date of Patent: Mar. 6, 1990

[54] ANTINEOPLASTIC AGENT-ENTRAPPING LIPOSOMES

[75] Inventors: Masayasu Kurono, Mie; Hitoshi Noda, Tajimi; Tomio Ogasawara, Kasugai; Hidefumi Yamakawa, Kasugai; Takafumi Iida, Kasugai; Kunio Yagi, Aichi, all of Japan

[73] Assignee: Kabushiki Kaisha Vitamin Kenkyusyo, Gifu, Japan

[21] Appl. No.: 153,302

[22] Filed: Feb. 8, 1988

[30] Foreign Application Priority Data

Feb. 9, 1987 [JP] Japan .................................. 62-26321

[51] Int. Cl.$^4$ ...................... A61K 37/22; A61J 5/00; B01J 13/02; B32B 5/16
[52] U.S. Cl. ................... 424/450; 428/402.2
[58] Field of Search .............. 264/4.1; 428/402.2, 428/402.21; 424/450

[56] References Cited

U.S. PATENT DOCUMENTS

| 4,544,545 | 10/1985 | Ryan et al. ................ | 424/450 X |
| 4,605,630 | 8/1986 | Kung et al. ................ | 264/4.6 X |
| 4,745,074 | 5/1988 | Schreier et al. ............ | 436/518 |
| 4,746,516 | 5/1988 | Moro et al. ................ | 424/450 |
| 4,756,910 | 7/1988 | Yagi et al. ................. | 424/450 |
| 4,766,046 | 8/1988 | Abra et al. ................. | 424/450 |
| 4,780,455 | 10/1988 | Lieberman et al. ......... | 514/77 |
| 4,822,777 | 4/1989 | Abra ......................... | 514/31 |
| 4,828,837 | 5/1989 | Uster et al. ................ | 424/450 |

OTHER PUBLICATIONS

Gabizon A. et al., "Liposome Formulations With Prolonged Circulation Time", *Proc. Natl. Acad. Sci. USA*, vol. 85, pp, 6949–6953, (1988).
Kurono et al., *Chem Abs.*, vol. 110, No. 18, "Antineoplastic Agent–Entrapping Liposomes", abs. #160396b.
Cullis et al., "Liposomes as Pharmaceuticals", in *Liposomes From Biophysics to Therapeutics*, Astro ed., Marcel Dekker, 1987, pp. 53–65.

*Primary Examiner*—John F. Terapane
*Assistant Examiner*—John M. Covert
*Attorney, Agent, or Firm*—Armstrong, Nikaido, Marmelstein, Kubovcik & Murray

[57] ABSTRACT

Some of antineoplastic agents, for instance, adriamycin and daunorubicin, have a positive charge at physiological pH. Such drugs possess high affinity for binding to steroidal sulfate by means of electrostatic force. The invention utilizes this property to prepare steroidal sulfate liposomes having a net negative charge and encapsulating the antineoplastic agent.

4 Claims, 4 Drawing Sheets

Peak: A: Adriamycin-entrapping liposomes with multi-layers
B: Adriamycin-entrapping small liposomes with a single layer
C: Free adriamycin ○——○ : Free adriamycin
●——● : PC : Chol : CholSO4=6:3:1, liposome entrapped adriamycin
△——△ : PC : CholSO4=9:1, liposome entrapped adriamycin ○—○ : Free adriamycin
●—● : PC:Chol:CholSO4=6:3:1,
liposome-entrapped adriamycin ○—○ : Free adriamycin
●—● : PC:Chol:CholSO4=6:3:1,
liposome-entrapped adriamycin ○—○: Free adriamycin
●—●: PC:Chol:CholSO₄=6:3:1, liposome entrapped adriamycin ○—○: Free adriamycin
●—●: PC:Chol:CholSO₄=6:3:1, liposome entrapped adriamycin

ANTINEOPLASTIC AGENT-ENTRAPPING LIPOSOMES

BACKGROUND OF THE INVENTION

1. Field of the Invention

The present invention relates to liposomes and more particularly to antineoplastic agent-entrapping liposomes.

2. Related Arts

As having been widely recognized, liposomes are lipid vesicles to be prepared by suspending a polar lipid film in an aqueous solution. These liposomes have basically the same structure as cell membranes in the living body and thus have been widely employed as a model for studying biological membranes. Further, studies have been made towards the application of liposomes as a vehicle or carrier for a drug or enzyme into the living body.

In case where the antineoplastic agent is entrapped within liposomes, the following advantages are expected:

1. Protection of the encapsulated agent from various metabolic enzymes,
2. Reduction of the essential toxicity of the antineoplastic agent,
3. Sustentation of pharmacological effect due to slow release,
4. Improvement in arrival to target tissues, and
5. Selective uptake into cytoplasm or lysosomes.

For example, adriamycin, one of the most active antineoplastic agents, is a glycosidic anthracycline antibiotic that is a fermentation product of the fungus, *Streptomyces peucetius* var. *caesius*. Adriamycin has a tetracycline ring structure with positively charged daunosamine attached by a glycosidic linkage. This drug is known to be useful for the treatment of leukemias and solid tumors; it attacks heart muscle, however, to cause irreversible injury. As a result, chronic cardiotoxicity has limited the clinical use of this drug for human.

Several workers have suggested an entrapment of adriamycin or its related anthracycline glycosides in negatively charged liposomes to reduce the cardiotoxicity and nephrotoxicity. In order to entrap adriamycin effectively, many kinds of negatively charged lipids have been utilized as the effective component of the liposomal membranes. Foressen et al. have shown that phosphatidylserine liposomes reduce the chronic cardiotoxicity. ["Proc. Natl. Acad. Sci. USA." 78, 1973-1877 (1981)], van Hoesel et al. have also observed reduction of the cardiotoxicity and nephrotoxicity when the drug in phosphatidylserine liposomes was administered ["Cancer Res." 44, 3698-3705 (1984)]. Rahman et al. demonstrated that chronic administration to beagle dogs of adriamycin entrapped in cardiolipin liposomes did not produce any cardiac abnormalities ["Cancer Res." 43, 5427-5432 (1983)]. Kojima et al. have shown that sulfatide liposomes gave the highest degree of adriamycin entrapment of all negatively charged lipids ["Biotechnol. Appl. Biochem". 8, 471-478 (1986)].

These negatively charged lipids as the effective component of the liposomal membranes are usually derived from natural materials, but the purification of these lipids is not easy; furthermore, complete synthesis of these lipids is complicated. As a result, these negatively charged lipids have proved to be expensive for clinical application of such liposomes; therefore, the mass production of antineoplastic agent-entrapping liposomes has been considered as unsuitable in terms of its manufacturing cost. On the other hand, instead of using these negatively charged lipids as components of liposomal membranes, synthetic anionic detergents may be adopted. Nevertheless, these detergents are not natural materials derived from the living body; and, for administration to man, safety requirements must be carefully established because most liposomes are primarily metabolized in the liver where they are taken up by the reticuloendothelial system. Accordingly, application of these detergents as a carrier for drugs has not been accepted in clinical field.

It would be desirable to satisfy the following requirements as an ideal liposome preparation that would provide an effectiveness, and suitable utilization of an antineoplastic agent such as adriamycin, daunorubicin or the like.

(a) The amount of agent entrapped in the liposomes is as large as possible; thus, the lipid dosage is at its minimum.
(b) The accumulation of agent in the heart and kidney is low so as to suppress the manifestation of cardiotoxicity and nephrotoxicity as much as possible.
(c) The applicable negatively charged lipids show a higher cost-performance to allow the mass production of antineoplastic agent-entrapping liposomes.
(d) The accumulation of the antineoplastic agent entrapped in liposomes in the liver is similar to the level of free antineoplastic agent, because the administration of a relatively large amount of the agent may cause adverse toxicity to the liver, and
(e) The concentration of agent is kept at a level high enough to attain a stable and sustaining manifestation of its pharmacological effect.

SUMMARY OF THE INVENTION

The present invention has four principal objects; viz., first is the provision of antineoplastic agent-entrapping liposomes at high yield; second is the maintenance of the drug concentration at a much higher blood level than can be achieved with the free drug; third is the reduction of essential toxicity of the drug; and last is the cost-performance to allow the mass production of antineoplastic agent-entrapping liposomes.

According to the invention, these objects can basically be attained by using steroidal sulfate as one of components for the liposomal membranes.

Namely, antineoplastic agent-entrapping liposomes according to the invention is characterized in that constitutional lipids thereof are phosphatidylcholine, cholesterol, and steroidal sulfate. The steroidal sulfate may be of that extracted from natural materials; in particular, cholesterol sulfate is a normal constituent of human erythrocytes and has been reported to have a protective effect against osmotic shock of the erythrocyte membrane [Bleau et al., "Biochim. Biophys. Acta." 352, 1-9 (1974)].

A synthesis of the steroidal sulfate can be attained by means of sulfation of steroids with sulfur trioxide/pyridine complex or chlorosulfonic acid [Sobel et al., "J. Am. Chem. Soc." 63, 1259-1261 (1942), or Goto et al., "Chem. Pharm. Bull." 27, 1926-1931 (1979)]. It can be synthesized easily and industrially in large quantities. It is considered that the administration of steroidal sulfate as a component of the liposomal membranes may be clinically safe because it is a natural material. Also, the cost is low because of the simple method used for its synthesis.

In addition to cholesterol sulfate, the sulfate esters of other steroids such as cholesterol, epicholesterol, cholestanol, ergosterol, lathosterol, 7-dehydrocholesterol, lanosterol, coprostanol, stigmasterol, β-sitosterol, and similar compounds can be prepared by esterification of the parent compound by the general methods as described above. Since steroidal sulfate esters have a negative charge at physiological pH, they are unstable in the ionized state. Therefore, it is necessary to add a counter-ion (cation), such as an alkali metal or an alkaline earth metal, particularly sodium ion.

Phosphatidylcholine, which is the main component of the antineoplastic agent-entrapping liposomes according to the invention, can also be synthesized. However, it is preferable to employ the same obtained from egg yolk, in view of its availability and the fact that its physical properties have been studied in greater detail than those of phosphatidylcholine obtained from other sources. Cholesterol, which is the other component of the liposomes, has a function to stabilize the liposomal membranes. In general, in case of high cholesterol content (more than 50 mol%) it is difficult to form stable liposomes. In case of a low content (less than 10 mol%) of steroidal sulfate, the liposomes entrap drugs or physiologically active substances at low yield. And in case of more than 30 mol%, the liposomal membranes are unstable. Therefore, a molar ratio of 50-90:10-50:10-30 for phosphatidylcholine, cholesterol, and steroidal sulfate is suitable for the preparation of the antineoplastic agent-entrapping liposomes according to the invention.

For the antineoplastic agent to be entrapped in the liposomes according to the invention, any drug can be selected, provided they do not inhibit liposome formation. Particularly desirable properties on the drug are a positive charge at physiological pH and easy dissolution in water. As such drugs, adriamycin, daunorubicin, cytarabine, vincristine, actinomycin D, mitomycin, bleomycin, acrarubicin, and the like may be listed and among them, adriamycin and daunorubicin are more preferable.

There is no specific limitation in the method of preparation for the antineoplastic agent-entrapping liposomes according to the invention, and thus various methods known per se can be utilized. In general, the liposomes are prepared by dissolving phosphatidylcholine, cholesterol, and a steroidal sulfate in an organic solvent in a flask, evaporating the solution of these lipids in vacuo to dryness to form a lipid film, adding an antineoplastic agent solution to swell the lipid film, shaking the flask vigorously to form a lipid suspension, sonicating the suspension to make liposomes, and removing the unentrapped agent by dialysis, gel filtration, or the like. As the organic solvent, chloroform, methanol and the like may be listed.

For adriamycin, an encapsulation efficiency in the liposomes is the order of 37 to 45% of the drug used. The efficiency is the same as that found by Kojima et al. ["Biotechnol. Appl. Biochem." 8, 471–478 (1986)] for liposomes containing sulfatide (i.e., 39 to 48%), who report that the encapsulation efficiencies of the liposomes containing sulfatide are higher than that of liposomes containing phosphatidylserine or cardiolipin.

One of the constitutional lipids for the liposomes according to the invention, namely, the steroidal sulfate enables the liposomes to entrap the antineoplastic agent at high yield, has a safety for living body as found those obtained from natural substances, and is easily available with a reasonable cost, since it may easily be synthesized.

Such advantageous facts of availability and cost on the raw material allow a mass production of the antineoplastic agent-entrapping liposomes according to the invention.

Further, the membranes of the antineoplastic agent-entrapping liposomes according to the invention are stable in the presence of saline or 75% human serum. The liposomes have also the following advantages: they do not cause hemolysis and do not induce platelet aggregation in vitro. When adriamycin-entrapping liposomes are given to mice, a concentration of the drug in the blood is kept at higher level than that in administration of free adriamycin. The accumulation in the spleen is higher, too, in the administration as the drug-entrapping liposomes. On the other hand, drug accumulation in the heart and kidney is lower, so that cardiotoxicity and nephrotoxicity might be reduced. Therefore, the present invention provides the liposomes that can entrap the antineoplastic agent at high yield, reduce toxicity in dosing, and might be safely used as drug carriers.

DETAILED DESCRIPTION OF THE PREFERRED EMBODIMENTS

Figure 1:
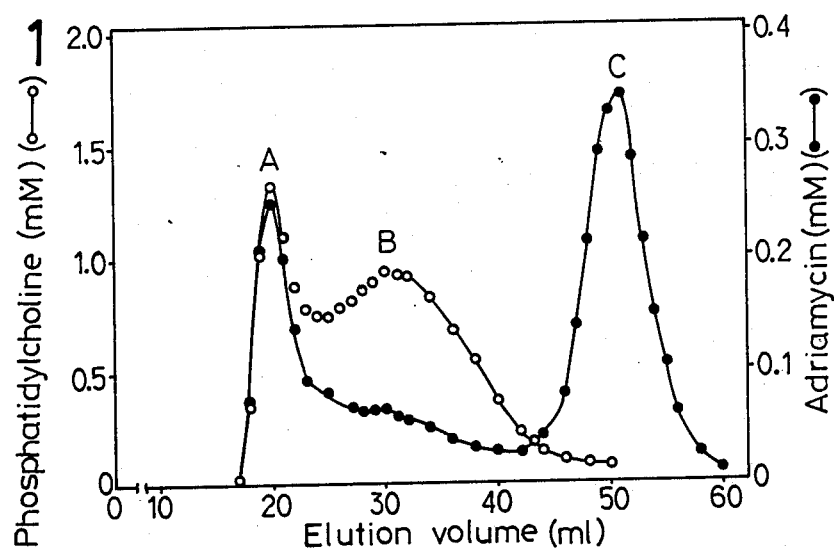
FIG. 1 is a graph showing an elution profile on a Sepharose CL-2B column for manufacturing a liposome preparation described in Example 1.

The invention will now be further explained with reference to Examples and Test Examples.

Materials used and analytical methods referred to in the Examples are as follows:

(a) Adriamycin ("Adriacin Inj.", registered Trademark in Japan) Marketed by Kyowa Hakko Kogyo Co., Ltd. of Tokyo, Japan.
(b) Phosphatidylcholine: Marketed by Nippon Fine Chemical Co., Ltd. of Osaka, Japan.
(c) Cholesterol: Marketed by Sigma Chemical Co. of St. Louis, U.S.A.
(d) Cholesterol sulfate: Synthesized by the method of Sobel et al. ["J. Am. Chem. Soc." 63, 1259–1261 (1941)].
(e) Saponin: Marketed by Nakarai Chemical Co., Ltd. of Kyoto, Japan (f) Adenosine 5'-diphosphate (ADP): Marketed by Sigma Chemical Co. of St. Louis, U.S.A.

(g) Soluble collagen: Marketed by Hormon-Chemie GmbH of Munchen, West Germany (h) Determination of adriamycin concentration: Adriamycin concentration was determined by the method described in "Cancer Chemother. Report" 54, 89–94 (1970).

(i) Determination of phosphatidylcholine concentration: Phosphatidylcholine concentration was determined by use of the reagent kit "Phospholipids B-Test Wako" (registered Trademark in Japan), marketed by Wako Pure Chemical Industries Co., Ltd. of Osaka, Japan.

EXAMPLE 1

Adriamycin-entrapping liposomes were prepared with phosphatidylcholine, cholesterol, and cholesterol sulfate in a molar ratio of 5:4:1 as follows:

25 μmol of phosphatidylcholine, 20 μmol of cholesterol, and 5 μmol of cholesterol sulfate were dissolved in chloroform in a round-bottom flask. Chloroform was removed with a rotary evaporator under a reduced pressure to form a lipid film on the surface of the flask, and the film was dried in vacuo. Then 5 μmol of adriamycin in 2.5 ml of saline was added to the flask, and the solution was shaken under a nitrogen atmosphere to swell the film and to prepare a lipid suspension. After the suspension was sonicated at 10°–17° C. for 50 min at 20 KHz and 35W by a probe-type sonicator (Model W-225R, manufactured by Heat Systems-Ultrasonics of Plainview, U.S.A.) under a nitrogen atomosphere, following three fractions were separated by gel-filtration with a Sepharose CL-2B (Pharmacia Biotechnology of Uppsala, Sweden) column.

(A) a turbid fraction containing large adriamycin-entrapping liposomes with multi-layers, (B) a clear fraction containing small adriamycin-entrapping liposomes with single-layer, and (C) free adriamycin fraction.

The small liposomes obtained with this preparation had an encapsulation efficiency of 45% for the starting adriamycin.

EXAMPLE 2

Adriamycin-entrapping liposomes were prepared with phosphatidylcholine, cholesterol, and cholesterol sulfate in a molar ratio of 6:3:1 as follows:

30 μmol of phosphatidylcholine, 15 μmol of cholesterol, and 5 μmol of cholesterol sulfate were dissolved in chloroform in a round-bottom flask. Chloroform was removed with a rotary evaporator under a reduced pressure to form a lipid film on inner surface of the flask. The film was dried in vacuo. Then 5 μmol of adriamycin in 2.5 ml of saline was added to the flask, and the solution was shaken under a nitrogen atmosphere to swell the film and to prepare a lipid suspension. The suspension was sonicated as in Example 1 to obtain a clear lipid dispersion. The dispersion was ultracentrifuged at 33,000 rpm for 1 hr. The supernatant was loaded onto gel-filtration column with Sepharose CL-6B (manufactured by Pharmacia Biotechnology of Uppsala, Sweden) in order to remove free adriamycin. The sizes of the liposomes obtained ranged from 25–55 nm in diameter, and small single-layer structures were observed by transmission electron microscopy of the liposomes stained negatively with 3% phosphotungstic acid.

TEST EXAMPLE 1

Stability of adriamycin-entrapping liposomes in saline

As in Example 2, adriamycin-entrapping liposomes were prepared with phosphatidylcholine, cholesterol, and cholesterol sulfate in a molar ratio of 6:3:1; and control liposomes were prepared with phosphatidylcholine and cholesterol sulfate in a molar ratio of 9:1. Stability of the liposomes in saline was examined.

The liposome suspension (0.1 mM adriamycin) in dialysis tube (pore size, 24 A) was incubated at 37° C. in saline. At various time intervals, adriamycin in the dialysate was determined.

A leakage of adriamycin was calculated as membrane permeability (%) according to an equation.

$$[C_t(V_s+V_l)/C_oV_l]\times 100$$

$C_o$, initial concentration of adriamycin in dialysis tube (μM);

$C_t$, concentration of adriamycin in the dialysate (μM);

$V_s$, volume of dialysate (ml);

$V_l$, volume of liposome suspension in dialysis tube (ml).

Figure 2:
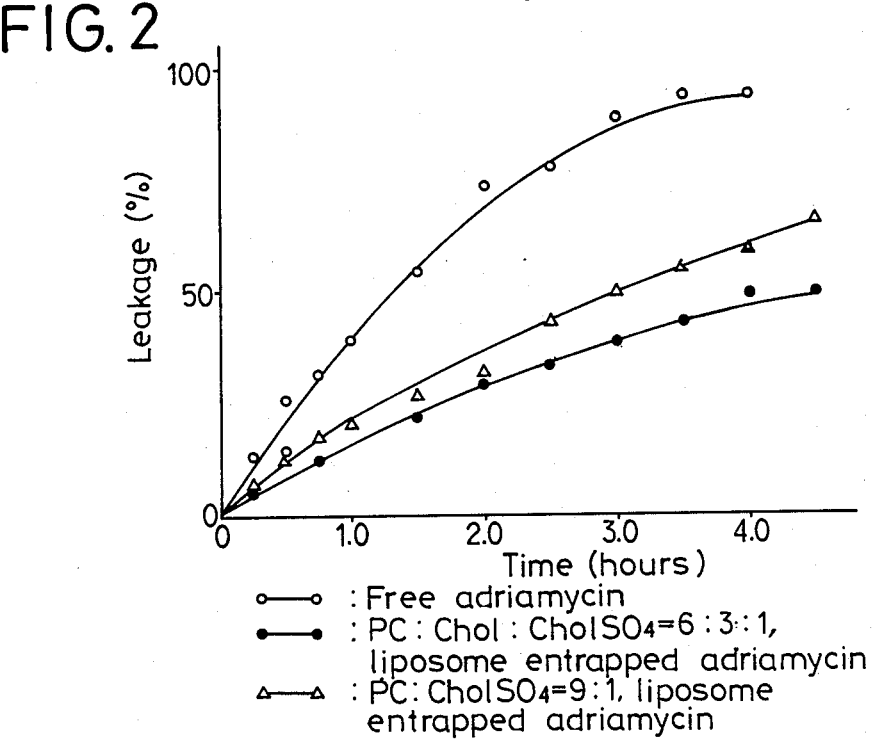
FIG. 2 is a graph showing leakage of adriamycin from the liposomes in saline at 37° C.

As seen from permeability curves in FIG. 2, the liposomes of the present invention have a good stability in saline.

TEST EXAMPLE 2

Stability of adriamycin-entrapping liposomes in 75% (v/v) human serum

Figure 3:
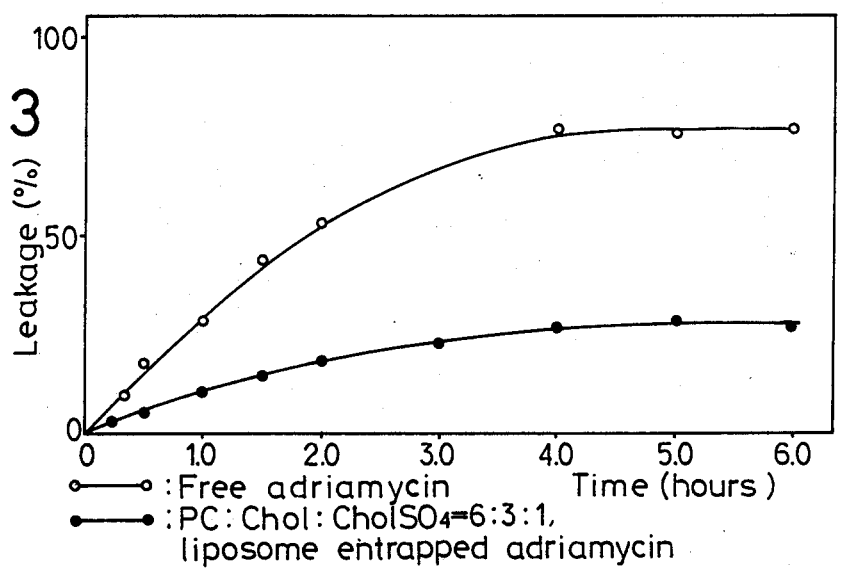
FIG. 3 is a graph showing leakage of adriamycin from the liposomes in 75% (v/v) human serum at 37° C.

Adriamycin-entrapping liposomes were prepared with phosphatidylcholine, cholesterol, and cholesterol sulfate in a molar ratio of 6:3:1, as in Example 2. Stability of the liposomes was examined in 75% human serum. The liposome suspension in dialysis tube (containing 75% human serum and having a pore size of 24 A) was incubated at 37° C. in 75% human serum. At various time intervals, adriamycin in the dialysate was determined according to the method of Odaka et al. ["Yakugaku Zasshi" 104, 620–623 (1984)]. A leakage of adriamycin was calculated as membrane permeability as in Test Example 1. As a control, free adriamycin solution was used in place of liposome suspension. As seen from permeability curves in FIG. 3, the liposomes of the present invention showed good stability in 75% human serum.

TEST EXAMPLE 3

Effects of adriamycin-entrapping liposomes on red blood cells

Two kinds of adriamycin-entrapping liposomes were prepared with phosphatidylcholine, cholesterol, and cholesterol sulfate in a molar ratio of 6:3:1 and 6:1:3, as in Example 2. Free adriamycin and saponin were used as positive control of hemolysis on red blood cells. Male Wistar rats weighing ca. 400 g were used for the experiment. Blood was collected from the abdominal aorta with sodium citrate (0.38% final concentration) as anticoagulant. Red blood cells were centrifuged at 3,000 rpm for 15 min at 4° C. and washed three times with saline, followed by dilution to a 10% suspension. The red blood cell suspension (50 μl) was added to the sample solution (1 ml) which had been pre-incubated at 37° C. for 5 min. The mixture was incubated at 37° C. for 1 hr with shaking. After centrifugation at 3,000 rpm for 15 min at 4° C., the optical density of the supernatant was measured at 540 nm.

Hemolysis ratio was calculated with saline to express 0% hemolysis and with distilled water as 100% hemolysis.

Free adriamycin and adriamycin-entrapping liposomes were examined at 575 nm. As seen from following Table 1, saponin at 80-100 μg/ml caused 100% hemolysis and free adriamycin at 0.25-2.0 mM exhibited slight hemolytic activity. While, the adriamycin-entrapping liposomes of the invention exhibited no hemolytic activity at all.

TABLE 1

| Sample | Concentration | Hemolysis (%) |
|---|---|---|
| ADM in liposomes | | |
| PC:Chol:CholSO$_4$ = 6:1:3 | 88 μM | N.D. |
| | 176 | N.D. |
| = 6:3:1 | 45 | N.D. |
| | 91 | N.D. |
| Free ADM | 125 | 0.7 |
| | 250 | 8.8 |
| | 500 | 15.5 |
| | 1000 | 20.4 |
| Saponin | 20 μg/ml | 0.3 |
| | 40 | 34.3 |
| | 60 | 73.0 |
| | 80 | 102 |
| | 100 | 105 |

PC, egg phosphatidylcholine; Chol, cholesterol;
CholSO$_4$, cholesterol sulfate.
N.D., not detected.

TEST EXAMPLE 4

Effects of adriamycin-entrapping liposomes on platelet aggregation

The adriamycin-entrapping liposomes described in Test Example 3 were utilized. Adriamycin was dissolved in saline, cholesterol sulfate in dimethylsulfoxide (DMSO), ADP in distilled water, and collagen in isotonic glucose solution (pH=2.7-2.9), respectively.

A male Wistar rat was anesthetized with ether and citrated blood was prepared from the rat abdominal aorta (final sodium citrate conc. was 0.38%). The blood was centrifuged at 1,000 rpm for 10 min at 4° C. for preparation of platelet-rich plasma, and further recentrifuged at 3,000 rpm for 10 min at 4° C. for preparation of platelet-poor plasma. After the pletelet-rich plasma was diluted with Isotone II solution (1:10,000), the number of platelets was counted by a Coulter counter (Model ZBI, manufactured by Coulter Electronics Co., Ltd. of Florida, U.S.A.); and the concentration was $(1.5\pm0.11)\times10^9$ platelets/ml of plasma (n=4).

Platelet aggregation was measured with an aggregometer (Sienco Corp. of Colorado, U.S.A.) at 37° C. by stirring at 1,000 rpm. 250 μl of platelet-rich plasma and 5, 10 or 50 μl of the samples were used. Platelet aggregation was calculated as a percentage of maximum aggregation, with platelet-poor plasma taken as 100%. The aggregometer was calibrated with platelet-poor plasma as 100% optical transmission and with platelet-rich plasma as 0% optical transmission. DMSO showed platelet aggregation activity below 30%.

As shown in following Table 2, both ADP [27.5±1.9% (n=4)] at 3.67 μM and collagen [54.1±3.5%(n=3)] at 9.8 μg/ml showed platelet aggregation activity.

But no aggregation was induced by free adriamycin, cholesterol sulfate ester, and adriamycin-entrapping liposomes of this invention.

TABLE 2

| Sample | Concentration | Aggregation (%) |
|---|---|---|
| ADM in liposomes | | |
| PC:Chol:CholSO$_4$ = 6:1:3 | 13.5 μM | N.D. |
| | 58.7 | N.D. |
| = 6:3:1 | 6.46 | N.D. |
| | 28.0 | N.D. |
| Free ADM | 76.9 | N.D. |
| | 333 | N.D. |
| CholSO$_4$ | 330 | N.D. |
| ADP | 3.67 | 27.5 ± 1.9(n = 4) |
| Collagen | 9.80 μg/ml | 54.1 ± 3.5(n = 3) |

PC, egg phosphatidylcholine; Chol, cholesterol; CholSO$_4$, cholesterol sulfate; ADP, adenosine-5'-diphosphate.
Platelet, $(1.15\pm0.11)\times10^9$/ml plasma.
N.D., not detected.

EXAMPLE 3

Adriamycin-entrapping liposomes with multi-layers were prepared with phosphatidylcholine, cholesterol, and cholesterol sulfate in a molar ratio of 6:3:1 as follows:

300 μmol of phosphatidylcholine, 150 μmol of cholesterol, and 50 μmol of cholesterol sulfate were dissolved in chloroform in a round-bottom flask, and the solvent was evaporated to dryness under a reduced pressure to form a lipid film on the surface of the flask. The film was dried in vacuo. Then, 50 μmol of adriamycin in 4 ml of saline was added to the flask, and it was shaken to swell the film and to prepare a lipid suspension. The suspension was sonicated at 20 kHz and 60 W for 10 min by a probe-type sonicator (Model W-375, manufactured by Heat Systems-Ultrasonics of Plainview, U.S.A.) in the 50% pulse-mode under a nitrogen atmosphere. The suspension was centrifuged at 3,000 rpm for 10 min. The supernatant was then applied to a Sepharose CL-2B column. The large liposomes with multi-layers were separated from the small liposomes with a single-layer and from free adriamycin.

TEST EXAMPLE 5

(Pharmacological Studies)

Male ddY mice weighing 22-30 g were used to evaluate an influence of adriamycin-entrapping liposomes on blood level and tissue disposition of the drug. Free or entrapped adriamycin prepared as in Example 3 was administered intravenously via a tail vein at a dose of 5 mg/kg. Animals were sacrificed at 5, 15, 30, 60, 120, 240, and 480 min, and at 24 hr following the drug administration. The blood was collected in a heparinized syringe. The liver, kidney, heart, and spleen were exised, rinsed with saline, and the liver was further perfused with saline. The blood and tissues were stored at −20° C. until analyzed.

The blood and tissues were analyzed for adriamycin content by the method of Rosso et al. ["Eur. J. Cancer" 8, 455-459 (1972)]. Tissues were homogenized in 5 volumes of ice-cold water with a Potter-Elvehjem homogenizer. To an aliquot of the homogenate or blood was added water to 2 ml. To each tube was then added 0.8 g of sodium chloride, and the resulting solution was heated at about 100° C. for 10 min. After chilling, 4 ml of n-butanol was added to the tubes. Then, the tubes were vigorously shaken for 15 min with a mechanical shaker and centrifuged at 3,000 rpm for 10 min. Adriamycin extracted in the upper layer was measured with a spectrofluorometer (Model 540-10 S, manufactured by Hitachi Ltd. of Tokyo, Japan) with an excitation at 470 nm and an emission at 590 nm.

To determine the efficiency of extraction, a known amount of adriamycin was added to the blood or each tissue and then adriamycin was extracted as described above. The efficiency of extraction from blood was 91% and from tissues, 52% to 100%.

FIGS. 4-8 show the pharmacological disposition of free and liposomal adriamycin following intravenous administration to mice at a dose of 5 mg/kg.

Figure 4:
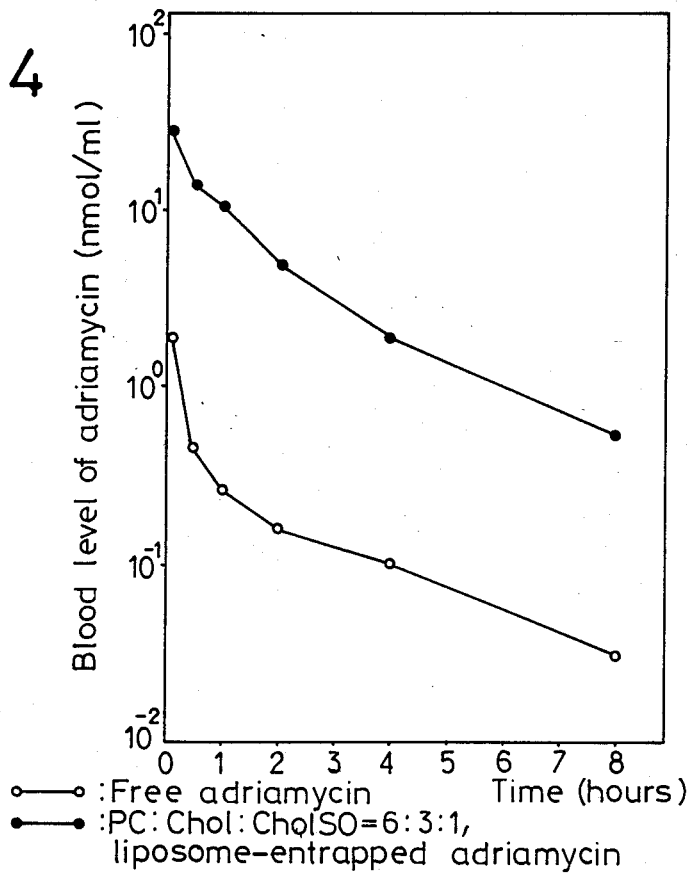
FIG. 4 is a graph showing blood level of free or liposome-entrapped adriamycin in normal mice which were used for pharmacological studies described in Example 4.
Figure 5:
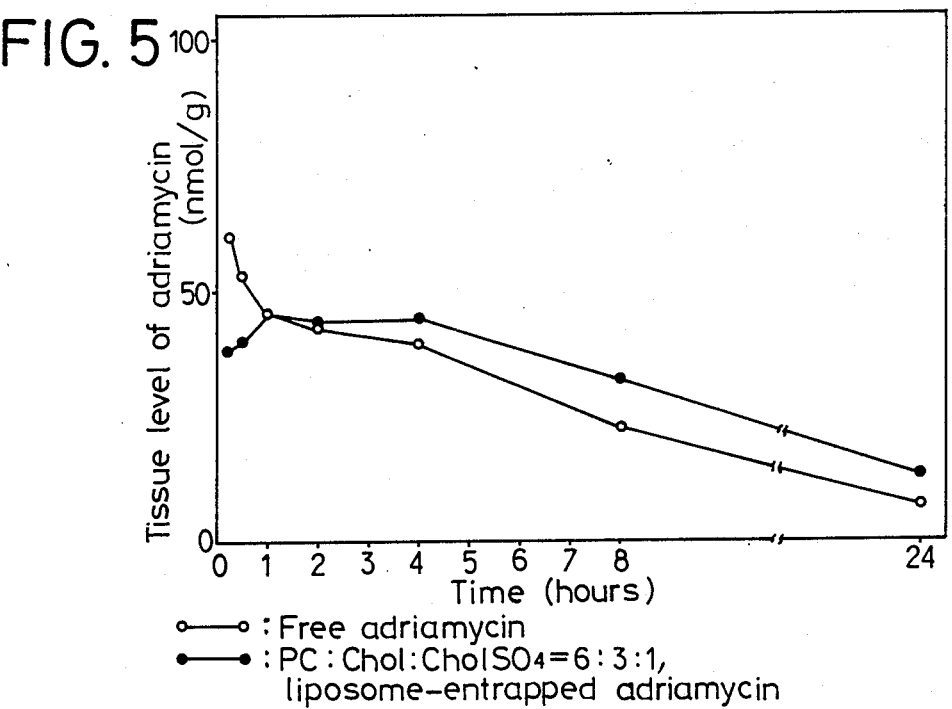
FIG. 5 is a graph showing adriamycin disposition in a mouse liver following intravenous administration of free or liposome-entrapped drug.
Figure 6:
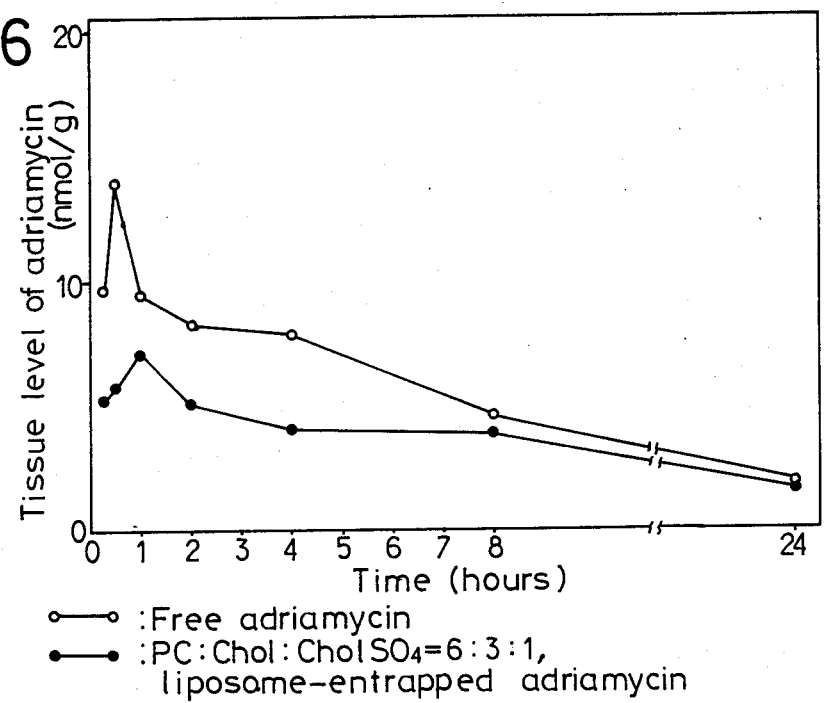
FIG. 6 is a graph showing adriamycin disposition in a mouse heart following intravenous administration of free or liposome-entrapped drug.
Figure 7:
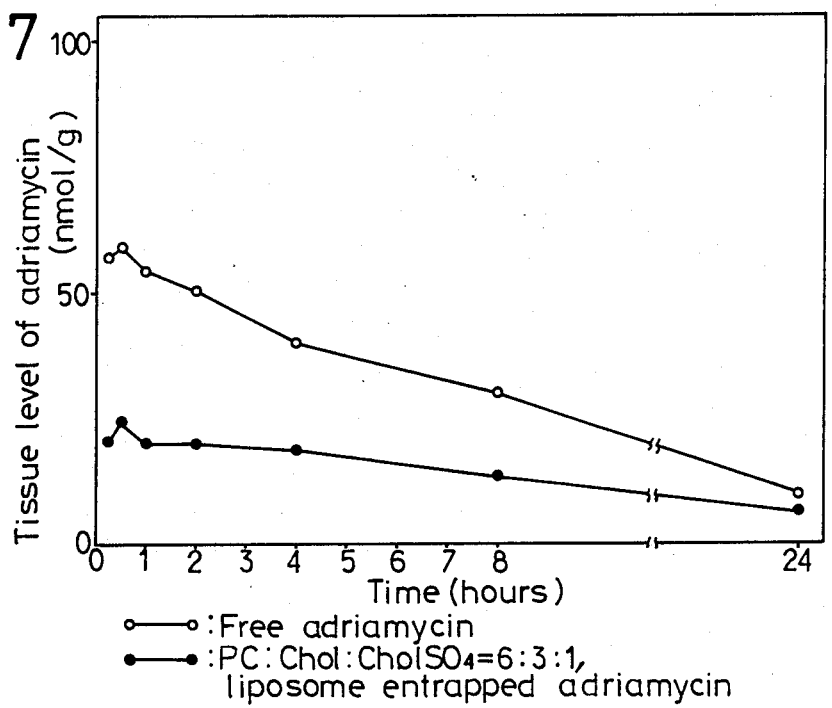
FIG. 7 is a graph showing adriamycin disposition in a mouse kidney following intravenous administration of free or liposome-entrapped drug.
Figure 8:
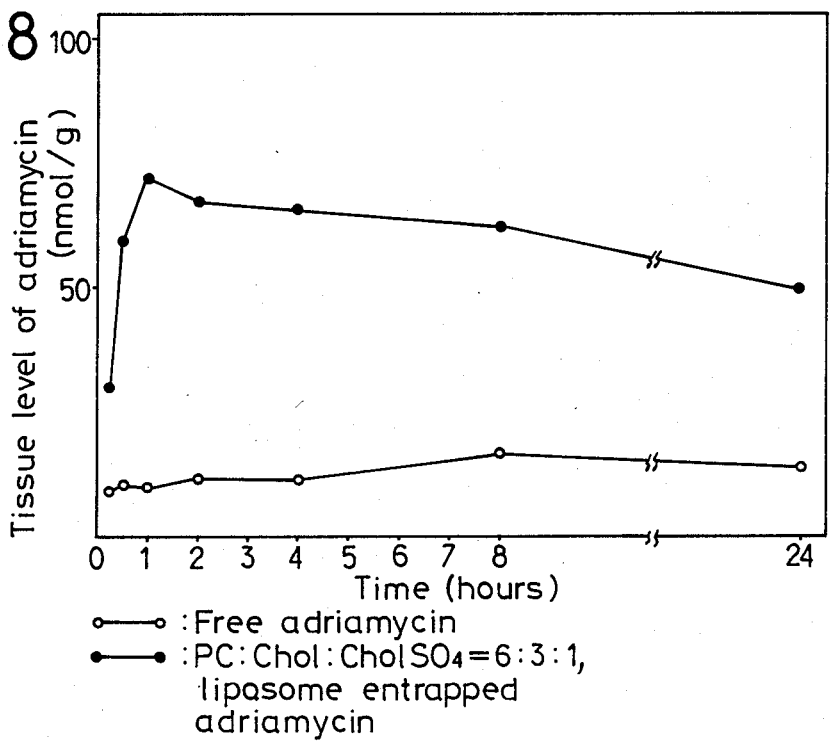
FIG. 8 is a graph showing adriamycin disposition in a mouse spleen following intravenous administration of free or liposome-entrapped drug.

The respective blood levels are shown in FIG. 4. The results are the average of the concentration of 3 animals. The peak blood level of adriamycin following free drug administration was 1.9 nmol/ml, whereas that with liposomal adriamycin was 27 nmol/ml.

The drug level in the spleen was 2-4 fold higher with liposomal adriamycin than with free adriamycin. On the contrary, the drug level in the kidney was at least 2-fold less with liposomal adriamycin than with free adriamycin. The level of adriamycin entrapped in the liposomes in the liver was similar to free adriamycin. In the heart, the peak of drug concentration of free drug occurred at 30 min and that of liposomal adriamycin occurred at 1 hr, the values being 14.0 and 7.0 nmol/g-wet weight, respectively. The drug level observed with liposomal adriamycin in the heart was half of those observed with free drug up to 4 hr. However, by 24 hr, the drug valve in the heart was more or less the same for both liposomal drug and free drug.

What is claimed is:

1. An antineoplastic composition comprising a liposome, the lipids constituting the liposome consisting essentially of phosphatidylcholine, cholesterol and a steroidal sulfate ester; and an antineoplastic agent entrapped in the liposome.

2. A composition according to claim 1, wherein the steroid sulfate ester is cholesterol sulfate.

3. A composition according to claim 1, wherein the antineoplastic agent is adriamycin.

4. A composition according to claim 2, wherein the antineoplastic agent is adriamycin.

* * * * *